(12) United States Patent
Greif et al.

(10) Patent No.: US 7,915,257 B2
(45) Date of Patent: Mar. 29, 2011

(54) USE OF TRIAZINETRIONE SULFONES FOR COMBATING COCCIDIOSIS

(75) Inventors: Gisela Greif, Remagen (DE); Iris Heep, Cologne (DE); Hans-Christian Mundt, Erkrath (DE)

(73) Assignee: Bayer Animal Health GmbH (DE)

( * ) Notice: Subject to any disclaimer, the term of this patent is extended or adjusted under 35 U.S.C. 154(b) by 820 days.

(21) Appl. No.: 10/362,038

(22) PCT Filed: Aug. 6, 2001

(86) PCT No.: PCT/EP01/09060
§ 371 (c)(1),
(2), (4) Date: Feb. 18, 2003

(87) PCT Pub. No.: WO02/14288
PCT Pub. Date: Feb. 21, 2002

(65) Prior Publication Data
US 2004/0013699 A1    Jan. 22, 2004

(30) Foreign Application Priority Data
Aug. 17, 2000    (DE) .................................. 100 40 174

(51) Int. Cl.
*A01N 43/66* (2006.01)
*A61K 31/53* (2006.01)
(52) U.S. Cl. ........................................ 514/241; 514/246
(58) Field of Classification Search ................... 424/405; 514/241, 246
See application file for complete search history.

(56) References Cited

U.S. PATENT DOCUMENTS

| | | | | |
|---|---|---|---|---|
| 3,966,725 | A | | 6/1976 | Reisdorf et al. ............... 260/248 |
| 4,255,231 | A | * | 3/1981 | Boba et al. ...................... 216/83 |
| 4,808,404 | A | * | 2/1989 | Bhogal ...................... 424/271.1 |
| 4,837,029 | A | * | 6/1989 | Olsen ........................ 514/252.13 |

FOREIGN PATENT DOCUMENTS

| | | |
|---|---|---|
| DE | 2413722 | 10/1975 |
| DE | 2532363 A1 | 2/1977 |
| DE | 2718799 | 11/1978 |
| EP | 0123217 | 10/1984 |
| GB | 1456964 | 12/1976 |
| WO | 9962519 | 12/1999 |
| WO | 0019964 | 4/2000 |
| WO | 0037084 | 6/2000 |

OTHER PUBLICATIONS

Gisela Greif et al., Chemotherapeutic approaches to protozoa: Coccidia—current level of knowledge and outlook, Parasitol Res (2001) 87: 973-975.
H.C. Mundt et al., Efficacy of various anticoccidials against experimental porcine neonatal isosporosis, Parasitol Res (2007) 100:401-411.
Milton M. McAllister et al., Dogs are definitive hosts of Neospora caninum, International Journal for Parasitology 28 (1998) 1473-1478.
R.J. Mackay et al., Equine protozoal myeoloencephalitis (EPM): Mystery wrapped in enigma, Diseases related to Protozoa and Possibilities for Treatment, Bayer Workshop at the 17th International Conference of the WAAVP, Aug. 15-19, 1999.
Bretislav Koudela et al., Role of acquired immunity and natural age resistance on the course of Isospora suis coccidiosis in nursing piglets, Diseases related to Protozoa and Possibilities for Treatment, Bayer Workshop at the 17th International Conference of the WAAVP, Aug. 15-19, 1999.
Gerhard Piekarski, Medical Parasitology, Springer-Verlag, pp. 1-3 and 77-88.
Peter L. Long, The Biology of the Coccidia, University Park Press, Baltimore, pp. 2-9.
H.C. Mundt et al., Control of Coccidiosis due to Eimeria bovis and Eimeria zuernii in Calves with Toltrazuril under Field Conditions in Comparison with Diclazuril and Untreated Controls, Parasitol Res (2007) 101:S93-S104.
Driesen, S.J. et al., "The Use of Toltrazuril for the Prevention of Coccidiosis in Piglets Before Weaning," Australian Veterinary Journal, Apr. 1995, vol. 72 No. 4, pp. 139-141.
Rommel, M., "Control of Non-Vector-Borne Protozoa," Int J of Parasitology, Feb. 1987, vol. 17 No. 2, pp. 639-647.
Haberkorn, A. and Mundt, H.-C., Praktische Tierarzt, 1988, vol. 69 No. 4, pp. 46, 49-51.
Lindsay et al., "Determination of the activity of ponazuril against Sarcocystis neurona in cell cultures," Veterinary Parasitology 92 (2000), pp. 165-169.

* cited by examiner

*Primary Examiner* — Yong S Chong

(57) ABSTRACT

The present invention relates to the use of specific derivatives of triazinetriones for controlling coccidioses in livestock, especially pigs.

3 Claims, No Drawings

USE OF TRIAZINETRIONE SULFONES FOR COMBATING COCCIDIOSIS

The present invention relates to the use of specific derivatives of triazinetriones for controlling coccidioses in livestock.

Coccidioses are infections which occur frequently in livestock and thus, for example, subclinical infections caused by protozoa of the genera coccidia, sarcosporidia and toxoplasma in pigs are spread worldwide. *Isospora suis* infections, for example, have, however, only in recent years been recognized as the cause of piglet diarrhoea and been researched very intensively. As a rule, infection takes place from the mother sow to the piglets or from piglet to piglet via oocysts each of which contain two sporocysts each with two sporozoites. The parasitic stages multiply in the epithelial cells of the villi of the small intestine, but extraintestinal stages have also been detected in the liver, spleen and lymph nodes. The clinical appearance of the disease includes a necrotic, inflammatory destruction of the intestinal epithelial cells and thus extensive interference with digestion and absorption. An acute disease is characterized by a watery, whitish or yellowish foul-smelling diarrhoea which usually occurs in week 2-3 of life. Infected piglets have a reduced weight gain. The treatment and therapy of the disease have not to date been adequately solved. Antibiotics are ineffective; although sulphonamides are recommended, therapy is usually too late. Other possibilities of treatment are contradictory: it was not possible to prevent disease by administering monensin, amprolium or furazolidone to experimentally infected piglets. In recent investigations it was possible to identify in some units, despite good hygiene, *Isospora suis* in up to 92% of all litters.

It is known from a number of publications, inter alia German Offenlegungsschriften 27 18 799, 25 090 37, 25 323 63, 24 137 22, WO 99/62519 that various derivatives of triazinetriones are suitable for controlling coccidioses in livestock.

It is also known from a number of publications, for example Driesen et al., Australian Vet. J., 72 (4) 139-141, 1995; Rommel, Int. J. of Parasit., 17(2), 639-647, 1987; Haberkorn and Mundt., Prakt. Tierarzt, 69 (4), 46, 49-51, 1988) that toltrazuril, a particular triazinetrione derivative, is suitable for treating coccidiosis (*Isospora suis*) in pigs.

Because of the wide variety of requirements to be met by modern pharmaceuticals, for example concerning level of activity, duration of action, spectrum of action, range of applications, toxicity, combination with other active ingredients, combination with formulation aids or synthesis, because of the possible occurrence of resistance, the development of such substances cannot, however, ever be regarded as complete, and there is a continuing great need for novel compounds which have advantages, at least in some aspects, over known compounds.

It has now been found that triazinetrione sulphones of the formula (I)

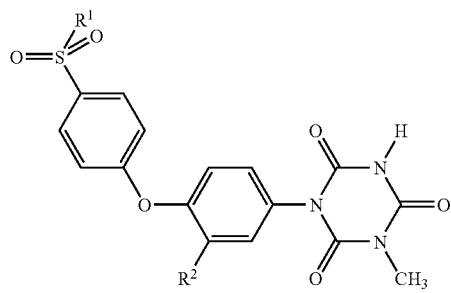

(I)

in which
$R^1$ represents halogenoalkyl,
$R^2$ represents alkyl, alkoxy, halogen or $SO_2N(CH_3)_2$, and their physiologically tolerated salts, have a very good coccidiocidal effect together with astonishingly low mammalian toxicity.

The compounds of the formula (I) can be obtained by the processes disclosed in German Offenlegungsschriften 27 18 799, 25 090 37, 25 323 63, 24 137 22, WO 99/62519.

The compounds of the formula (I) show when used according to the invention for treating coccidioses in livestock a mammalian toxicity which is surprisingly low compared with compounds known in the state of the art, and are therefore clearly superior to the known compounds in this use.

Compounds of the formula (I) employed for the use in controlling coccidioses in livestock are preferably those in which
$R^1$ represents $C_1$-$C_4$-halogenoalkyl with 1 to 5 halogen atoms,
$R^2$ represents $C_1$-$C_4$-alkyl, $C_1$-$C_4$-alkoxy, halogen or $SO_2N(CH_3)_2$, and their physiologically tolerated salts.

Compounds of the formula (I) particular preferably employed according to the invention are those in which
$R^1$ represents $C_1$-$C_4$ halogenoalkyl with 1 to 5 halogen atoms,
$R^2$ represents $C_1$-$C_4$-alkyl, and their physiologically tolerated salts.

Compounds of the formula (I) very particularly preferably employed according to the invention are those in which
$R^1$ represents $C_1$-$C_4$ perhalogenoalkyl,
$R^2$ represents methyl or ethyl, and their physiologically tolerated salts.

In particular, the use of the compound of the formula

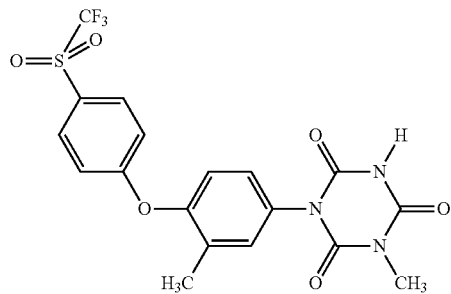

with the name ponazuril is very particularly preferred.

The compounds of the formula (I) may, where appropriate, depending on the nature and number of the substituents be in the form of geometric and/or optical isomers or regioisomers or mixtures of such isomers of varying composition. Both the use of the pure isomers and of the mixtures of isomers are claimed according to the invention.

Compounds which are preferred, particularly preferred or very particularly preferred etc. are those which have the substituents mentioned below as preferred, particularly preferred or very particularly preferred etc.

Preferred among the halogenoalkyl radicals indicated in the definition of $R^1$, including those mentioned as preferred, particularly preferred, very particularly preferred, are in each case in turn the fluoroalkyl radicals.

The radical definitions and explanations stated above in general or stated in preferred ranges can, however, also be combined as desired with one another, that is to say between the respective ranges and preferred ranges.

The compounds according to the invention can for the use according to the invention against coccidiosis be converted into all conventional formulations and be administered in various administration forms. Oral administrations are preferred in this connection, in particular administration as oral aqueous suspension.

Preferred dosages are 1-500 mg of active ingredient per kg of body weight of the animal to be treated, particularly preferred dosages are from 10 to 200 mg/kg and very particularly preferred dosages are 20-100 mg/kg.

Preparations suitable for livestock are:
solutions such as solutions for injection, oral solutions, concentrates for oral administration after dilution, solutions for use on the skin or in body cavities, pour-on formulations, gels;
emulsions and semisolid preparations for oral or cutaneous use and for injection; examples of semisolid preparations are suspensions, pastes.
Formulations in which the active ingredient is processed in an ointment base or in an oil-in-water or water-in-oil emulsion base;
solid preparations such as powders, premixes or concentrates, granules, pellets, tablets, boluses, capsules; aerosols and inhalations.

Solutions for injection are administered intravenously, intramuscularly and subcutaneously.

Solutions for injection are prepared by dissolving the active ingredient in a suitable solvent and possibly adding additions such as solubilizers, acids, bases, buffer salts, antioxidants, preservatives. The solutions are sterilized by filtration or, if necessary, prepared aseptically and bottled.

Solvents which may be mentioned are: physiologically tolerated solvents such as water, alcohols such as ethanol, butanol, benzyl alcohol, glycerol, propylene glycol, polyethylene glycols, N-methylpyrrolidone, glycerol formal, solketal (=isopropylideneglycerol), dimethylacetamide, 2-pyrrolidone, tetraglycol (=polyethylene glycol ether of tetrahydrofurfuryl alcohol) and mixtures thereof.

The active ingredients can, where appropriate, also be dissolved in physiologically tolerated vegetable or synthetic oils suitable for injection.

Solubilizers which may be mentioned are: solvents which promote the dissolving of the active ingredient in the main solvent or prevent its precipitation. Examples are polyvinylpyrrolidone, polyethoxylated castor oil, polyethoxylated sorbitan esters.

Examples of preservatives are: benzyl alcohol, trichlorobutanol, p-hydroxybenzoic esters, n-butanol, and organic acids with preserving properties such as benzoic acid, propionic acid or sorbic acid and salts thereof. The preservatives may, where appropriate, also be employed as combination of two or more agents.

Oral solutions are used directly. Concentrates are used orally after previous dilution to the use concentration. Oral solutions and concentrates are prepared as described above for injection solutions, it being possible to dispense with sterile operations.

Solutions for use on the skin or body cavities are poured on, painted on, rubbed in, sprayed on or used for dips. These solutions are prepared as described above for solutions for injection. It is particularly advantageous to add thickeners during preparation.

Thickeners are: inorganic thickeners such as bentonites, colloidal silica, aluminium monostearate, organic thickeners such as cellulose derivatives, polyvinyl alcohols and their copolymers, acrylates and methacrylates, xanthans.

Gels are applied to or spread on the skin or introduced into body cavities. Gels are prepared by mixing solutions which have been prepared as described for solutions for injection with sufficient thickener to result in a clear composition with an ointment-like consistency. The thickeners applied are the thickeners indicated hereinbefore.

Pour-on formulations are poured or sprayed on to limited areas of the skin, in which case the active ingredient either penetrates through the skin and has a systemic action or is distributed on the surface of the body.

Pour-on formulations are prepared by dissolving, suspending or emulsifying the active ingredient in suitable solvents or mixtures of solvents which are compatible with skin. Further excipients such as colorants, absorption-promoting substances, antioxidants, light stabilizers, adhesives are added where appropriate.

Solvents which may be mentioned are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate;

Ethers such as alkylene glycol alkyl ethers such as dipropylene glycol monomethyl ether, diethylene glycol monobutyl ether, ketones such as acetone, methyl ethyl ketone, aromatic and/or aliphatic hydrocarbons, vegetable or synthetic oils, DMF, dimethylacetamide, N-methylpyrrolidone, 2,2-dimethyl-4-hydroxymethyl-1,3-dioxolane.

Colorants are all colorants which are approved for use on livestock and which can be dissolved or suspended.

Absorption-promoting substances are DMSO, spreading oils such as isopropyl myristate, dipropylene glycol pelargonate, silicone oils, fatty acid esters, triglycerides, fatty alcohols.

Antioxidants are sulphites or metabisulphites such as potassium metabisulphite, ascorbic acid, butylated hydroxytoluene, butylated hydroxyanisole, tocopherol.

Examples of light stabilizers are substances from the class of benzophenones or novantisolic acid.

Examples of adhesives are cellulose derivatives, starch derivatives, polyacrylates, natural polymers such as alginates, gelatin.

Emulsions can be used orally, cutaneously or as injection.
Emulsions are either of the water-in-oil type or of the oil-in-water type.

They are prepared by dissolving the active ingredient in one phase and homogenizing the latter with the assistance of suitable emulsifiers and, where appropriate, further excipients such as colorants, absorption-promoting substances, preservatives, antioxidants, light stabilizers, viscosity-increasing substances.

Mention may be made of the following as hydrophobic phase (oils): paraffin oils, silicone oils, natural vegetable oils such as sesame oil, almond oil, castor oil, synthetic triglycerides such as caprylic/capric acid biglyceride, triglyceride mixture with vegetable fatty acids of chain length $C_{8-12}$ or other specially selected natural fatty acids, partial glyceride mixtures of saturated or unsaturated, possibly also hydroxyl group-containing fatty acids, mono- and diglycerides of $C_8/C_{10}$-fatty acids.

Fatty acid esters such as ethyl stearate, di-n-butyryl adipate, hexyl laurate, dipropylene glycol perlargonate, esters of a branched fatty acid of medium chain length with saturated fatty alcohols of chain length $C_{16}$-$C_{18}$, isopropyl myristate, isopropyl palmitate, caprylic/capric esters of saturated fatty alcohols of chain length $C_{12}$-$C_{18}$, isopropyl stearate, oleyl oleate, decyl oleate, ethyl oleate, ethyl lactate, waxy fatty acid esters such as artificial duck preen gland oil, dibutyl phthalate, diisopropyl adipate, ester mixtures related to the latter inter alia.

Fatty alcohols such as isotridecyl alcohol, 2-octyldodecanol, cetylstearyl alcohol, oleyl alcohol.

Fatty acids such as, for example, oleic acid and mixtures thereof.

Mention may be made of the following as hydrophilic phase:
  water, alcohols such as, for example, propylene glycol, glycerol, sorbitol and mixtures thereof.

Mention may be made of the following as emulsifiers: surfactants (including emulsifiers and wetting agents), such as
  1. nonionic, for example polyethoxylated castor oil, polyethoxylated sorbitan monooleate, sorbitan monostearate, ethyl alcohol, glycerol monostearate, polyoxyethyl stearate, alkylphenol polyglycol ether,
  2. ampholytic such as di-Na N-lauryl-β-iminodipropionate or lecithin,
  3. anionic such as Na-lauryl sulphate, fatty alcohol ether sulphates, mono/dialkyl polyglycol ether orthophosphoric ester monoethanolamine salt,
  4. cationic such as cetyltrimethylammonium chloride.

Further suitable excipients are:
  viscosity-increasing and emulsion-stabilizing substances such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silica or mixtures of the substances mentioned.

Suspensions can be used orally, cutaneously or as injection. They are prepared by suspending the active ingredient in a liquid vehicle where appropriate with addition of further excipients such as wetting agents, antifoams, colorants, absorption-promoting substances, suspension stabilizers, preservatives, antioxidants, light stabilizers, humectants.

Mention may be made as preferred of suspensions which can be administered orally and contain:
  A) compounds of the formula (I) in concentrations of from 0.1 to 30% by weight, particularly preferably from 1 to 10% by weight.
  B) suspension stabilizers such as, for example, bentonites and/or xanthans in concentrations each of from 0.01 to 5% by weight, particularly preferably from 0.05 to 1% by weight.
  C) where appropriate ionic or nonionic wetting agents in concentrations of from 0.01 to 5% by weight, particularly preferably from 0.1 to 0.5% by weight.
  D) where appropriate antifoams based, for example, on silicones in concentrations of from 0.01 to 5% by weight, particularly preferably from 0.05 to 0.5% by weight.
  E) where appropriate humectants in concentrations of from 1 to 30% by weight, particularly preferably from 5 to 20% by weight.
  F) where appropriate preservatives or else combinations thereof in concentrations of from 0.001 to 5% by weight, particularly preferably from 0.1 to 0.5% by weight.
  G) where appropriate acidic or basic substances in the concentrations necessary to adjust the pH.

Liquid vehicles which may be mentioned are the solvents and homogeneous mixtures of solvents mentioned hereinbefore as long as they are pharmaceutically acceptable and the active ingredient or active ingredients dissolve therein to only a small extent or not at all. Water is preferably used.

Wetting agents (dispersants) which may be mentioned for the suspensions which can be administered orally are surfactants such as
  1. anionic such as Na lauryl sulphate, fatty alcohol ether sulphates, mono/dialkyl polyglycol ether orthophosphoric ester monoethanolamine salt, ligninsulphonates or dioctyl sulphosuccinate,
  2. cationic such as cetyltrimethylammonium chloride,
  3. ampholytic such as di-Na N-lauryl-β-iminodipropionate or lecithin,
  4. nonionic, for example polyethoxylated castor oil, polyethoxylated sorbitan monooleate, sorbitan monostearate, ethyl alcohol, glycerol monostearate, polyoxyethylene stearate, alkylphenol polyglycol ether, Pluronic®.

Suitable antifoams are those based on silicones, for example dimethicone or simethicone.

Suspension stabilizers which can be employed are, for example, the viscosity-increasing substances mentioned hereinbefore.

It is possible to employ conventional humectants, and examples which may be mentioned are: propylene glycol, glycerol, sugar alcohols such as sorbitol, sugars such as sucrose.

Suitable preservatives are known to the skilled person; examples have already been mentioned hereinbefore. Organic acids with preserving properties are preferably employed, such as, for example, benzoic acid, propionic acid or sorbic acid and salts thereof. The preservatives can also be employed as combination of two or more agents, and a preferred example which may be mentioned is a combination of sodium propionate and sodium benzoate.

Suitable acidic or basic substances for adjusting the pH are conventional pharmaceutically acceptable acids, bases and buffers.

Acids which may be mentioned are, for example: hydrochloric acid, citric acid and tartaric acid. Examples of bases which may be mentioned are: alkali metal hydroxides such as sodium hydroxide and potassium hydroxide; alkali metal and alkaline earth metal carbonates such as sodium carbonate, and amines, for example mono-, di- or triethanolamine.

Examples of suitable buffer systems are those based on phosphates.

The pH is preferably in the range from 2 to 10, in particular 3 to 7.

The active ingredient is preferably employed in micronized form in the suspensions, normally in particle size distributions of from 0.1 to 100 µm, preferably 1 to 50 µm.

Further excipients which may be mentioned are those indicated hereinbefore.

Pastes can be administered orally or cutaneously. They differ from the mobile to viscous suspensions and emulsions described above by their higher viscosity. Pastes containing ponazuril (=toltrazuril sulphone) have already been described in WO 99/62519.

Those which may be mentioned as preferred are pastes which can be administered orally and contain compounds of the formula (I), which are characterized in that
  a) the active ingredient is present in a particle size of $1 \times 10^{-6}$ m and a maximum particle size of $50 \times 10^{-6}$ m in a concentration of 0.1-20% by weight,
  b) polyacrylic acids with an acrylic acid content of from 56 to 68% by weight and a molecular weight of about $3 \times 10^6$, which are neutralized with alkali metal or alkaline earth metal bases, are present in a concentration of 0.1-5% by weight,
  c) where appropriate humectants are present in a concentration of from 5 to 30% by weight, d) where appropriate preservatives are present in a concentration of from 0.01 to 0.5% by weight,
e) and the remainder in 100% by weight is made up with water.

The active ingredient is present in the said pastes preferably in concentrations by weight of from 5% by weight to 20% by weight, particularly preferably from 10% by weight to 15% by weight.

The polyacrylic acids used in the said pastes are preferably neutralized with alkali metal hydroxide or carbonate. Polyacrylic acids are present in the formulation according to the invention in concentrations by weight of from 0.2% to 1%, preferably of 0.5%. These are commercially available and known in pharmacopoeias for example under the proprietary name Carbomer 934 P.

Preferred preservatives in the said pastes are para-hydroxybenzoic esters (parabens) such as methyl 4-hydroxybenzoate, ethyl 4-hydroxybenzoate or propyl 4-hydroxybenzoate. The preservatives can be employed singly or in combination for adequate preservation. They are normally present in concentrations of 0.01-0.5% by weight.

It is optionally possible for the said pastes also to contain humectants such as, for example, glycerol or 1,2-propylene glycol. Humectants are employed in concentrations by weight of from 5% to 30%, preferably from 10% to 20%.

The active ingredient is present in the said pastes in a particle size of from 1 to $10 \times 10^{-6}$ m, preferably from 1 to $5 \times 10^{-6}$ m. The maximum of the particle size is $50 \times 10^{-6}$ m, preferably $30 \times 10^{-6}$ m. The particle sizes are determined by laser scattering measurement (for example with a Malvern Mastersizer). The paste is obtained by mixing the individual components. Its consistency can be altered by increasing or decreasing the water content. A pasty consistency is desired. This permits oral administration of the composition with suitable applicators such as syringes, tubes, spatulas etc.

To prepare solid preparations, the active ingredient is mixed with suitable carriers, where appropriate with the addition of excipients, and converted into the desired shape.

Carriers which may be mentioned are all physiologically tolerated solid inert substances. Inorganic and organic substances are used as such. Examples of inorganic substances are sodium chloride, carbonates such as calcium carbonate, hydrogen carbonates, aluminium oxides, silicas, aluminas, precipitated or colloidal silicon dioxide, phosphates.

Examples of organic substances are sugars, cellulose, human and animal foods such as milk powder, animal meals, ground and crushed grains, starches.

Excipients are preservatives, antioxidants, colorants, which have already been mentioned hereinbefore.

Further suitable excipients are lubricants and glidants such as, for example, magnesium stearate, stearic acid, talc, bentonites, disintegration-promoting substances such as starch or crosslinked polyvinylpyrrolidone, binders such as, for example, starch, gelatin or linear polyvinylpyrrolidone, and dry binders such as microcrystalline cellulose.

The active ingredients can also be in the form of their encapsulated solid or liquid formulations mentioned above.

The active ingredients can also be used in the form of an aerosol. For this purpose, the active ingredient is finely dispersed in a suitable formulation under pressure.

It may also be advantageous to use the active ingredients in formulations which release the active ingredient in a delayed manner.

The active ingredients are preferably administered together with the feed and/or the drinking water.

The feed includes feedstuff ingredients of vegetable origin such as hay, beets, cereals, cereals by-products, feedstuff ingredients of animal origin such as meat, fats, dairy products, bone meal, fish products, also feedstuff ingredients such as vitamins, proteins, amino acids, for example DL-methionine, salts such as calcium carbonate and sodium chloride. The feed also includes supplementary, formulated and compounded feedstuffs. These contain feed ingredients in a composition which ensures a balanced diet in terms of energy and protein supply and the supply of vitamins, mineral salts and trace elements.

The concentration of the active ingredients in the feed is normally about 0.01 to 500 ppm, preferably 0.1 to 50 ppm.

The active ingredients can be added as such or in the form of premixes or feed concentrates to the feed.

Premixes and feed concentrates are mixtures of the active ingredient with a suitable carrier.

The carriers include feedstuff ingredients or mixtures thereof.

They may additionally contain further aids such as, for example, substances which control the flow properties and mixing properties, such as, for example, silicas, bentonites, ligninsulphonates. It is additionally possible to add antioxidants such as BHT or preservatives such as sorbic acid or calcium propionate.

Concentrates for administration via the drinking water must be formulated so that a clear solution or a stable homogeneous suspension is produced on mixing with the drinking water.

Suitable carriers are therefore water-soluble substances (feed additives) such as sugars or salts (for example citrates, phosphates, sodium chloride, Na carbonate).

They may likewise contain antioxidants and preservatives.

The active ingredients are suitable, while having a surprisingly low toxicity for warm-blooded species, for the control according to the invention of parasitic protozoa which occur in livestock management and livestock breeding among agricultural and breeding livestock, zoo, laboratory and experimental animals and pets. They are moreover effective against all or individual stages of development of the pests and against resistant and normally sensitive strains. Control of the parasitic protozoa is intended to reduce disease, deaths and reductions in performance (for example in the production of meat, milk, wool, hides, eggs, honey etc) so that more economic and easier livestock management is possible through use of the active ingredients.

The parasitic protozoa include:

Mastigophora (Flagellata) such as, for example, Trypanosomatidae, for example *Trypanosoma brucei, T. gambiense, T. rhodesiense, T. congolense, T. cruzi, T. evansi, T. equinum, T. lewisi, T. percae, T. simiae, T. vivax, Leishmania brasiliensis, L. donovani, L. tropica*, such as, for example, Trichomonadidae, for example *Giardia lamblia, G. canis*.

Sarcomastigophora (Rhizopoda) such as Entamoebidae for example *Entamoeba histolytica*, Hartmanellidae for example *Acanthamoeba* sp., *Hartmanella* sp.

Apicomplexa (Sporozoa) such as Eimeridae for example *Eimeria acervulina, E. adenoides, E. alabahmensis, E. anatis, E. anseris, E. arloingi, E. ashata, E. aubumensis, E. bovis, E. brunetti, E. canis, E. chinchillae, E. clupearum, E. columbae, E. contorta, E. crandalis, E. debliecki, E. dispersa, E. ellipsoidales, E. falciformis, E. faurei, E. flavescens, E. gallopavonis, E. hagani, E. intestinalis, E. iroquoina, E. irresidua, E. labbeana, E. leucarti, E. magna, E. maxima, E. media, E. meleagridis, E. meleagrimitis, E. mitis, E. necatrix, E. ninakohlyakimovae, E. ovis, E. parva, E. pavonis, E. perforans, E. phasani, E. piriformis, E. praecox, E. residua, E. scabra, E. spec., E. stiedai, E. suis, E. tenella, E. truncata, E.*

*truttae, E. zuemii, Globidium* spec., *Isospora belli, I. canis, I. felis, I. ohioensis, I. rivolta, I.* spec., *I. suis, Neospora caninum, N. hugesi, Cystisospora* spec., *Cryptosporidium* spec. such as Toxoplasmadidae for example *Toxoplasma gondii*, such as Sarcocystidae for example *Sarcocystis bovicanis, S. bovihominis, S. neurona, S. ovicanis, S. ovifelis*, S. spec., *S. suihominis* such as Leucozoidae for example *Leucozytozoon simondi*, such as Plasmodiidae for example *Plasmodium berghei, P. falciparum, P. malariae, P. ovale, P. vivax*, P. spec., such as Piroplasmea for example *Babesia argentina, B. bovis, B. canis*, B. spec., *Theileria parva, Theileria* spec., such as Adeleina for example *Hepatozoon canis, H.* spec.

In addition Myxospora and Microspora, for example *Glugea* spec. *Nosema* spec.

In addition *Pneumocystis carinii*, and Ciliophora (Ciliata) such as, for example, *Balantidium coli, Ichthiophthirius* spec., *Trichodina* spec., *Epistylis* spec.

The compounds according to the invention are also effective against protozoa which occur as parasites on insects. Those which may be mentioned are parasites of the phylum Microsporida, in particular of the genus *Nosema*. Particular mention may be made of *Nosema apis* in the honeybee.

Protozoa which should be very particularly emphasized are those of the genera and species which lead to subclinical infections in pigs, in particular: *Trypanosoma congolense simae, T. vivax vivax, T. congolense congolense, T. brucei evansi, Tritrichomonas suis, Trichomitus rotunda, Tetratrichomonas buttreyi, Eimeria debliecki, E. suis, E. scabra, E. perminuta, E. spinosa, E. polita, E. porci, E. neodebliecki, Isospora suis, Cryptosporidium, Toxoplasma gondii, Sarcocystis miescheriana, S. suihominis, Babesia trautmanni, B. perroncitoi, Balantidium coli*.

The agricultural and breeding livestock include mammals such as, for example, cattle, horses, sheep, pigs, goats, camels, water buffalo, donkeys, rabbits, fallow deer, reindeer, fur-bearing animals such as, for example, mink, chinchilla, racoon, birds such as, for example, chicken, geese, turkeys, ducks, pigeons, bird species for keeping at home and in zoos. They also include useful and ornamental fish. Pigs of all species, subspecies and breeds should be particularly emphasized in this connection.

Laboratory and experimental animals include mice, rats, guinea pigs, golden hamsters, dogs and cats.

Pets include dogs and cats.

The fish include useful, breeding, aquarium and ornamental fish of all ages which live in fresh and salt water. The useful and breeding fish include, for example, carp, eel, trout, white fish, salmon, bream, roach, rudd, chub, sole, plaice, halibut, Japanese yellowtail (*Seriola quinqueradiata*), Japanese eel (*Anguilla japonica*), red sea bream (*Pagurus major*), sea bass (*Dicentrarchus labrax*), grey mullet (*Mugilus cephalus*), pompano, gilthead sea bream (*Sparus aurata*), Tilapia spp., chichlid species such as, for example, plagioscion, channel catfish. The compositions according to the invention are particularly suitable for treating fry, for example carp with a body length of from 2 to 4 cm. The compositions are also very suitable in eel growing.

The following examples are intended to illustrate the invention without, however, restricting it:

Investigations of the Efficacy of Ponazuril Compared with Toltrazuril

A. Efficacy of Ponazuril on Artificially Induced Infections of Chickens with *Eimeria tenella, E. maxima* and *E. acervulina*:

The aim of this investigation was to test ponazuril for efficacy for an artificial mixed infection (*Eimeria tenella, E. maxima* and *E. acervulina*) in chickens under cage housing conditions.

Groups each of 44 birds (4 replicates per treatment of 11 birds in each case) were formed and, on day 14, infected with sporulated oocysts. Ponazuril was administered each day on day 10-24 or 17-24. Three dosages in the feed were used in both treatment periods: 5 ppm, 10 ppm and 20 ppm. The result of the treatment was determined by various clinical and parasitological parameters, including the mortality caused by the coccidiosis and the oocyst excretion in the faeces.

The infection was moderate to extensive. The mortality caused by the coccidiosis was 20% of the untreated controls. It was possible to control the infection with all dosages and treatment schedules. The degree of control depended directly on the dosage and the start of the treatment. An early start of the treatment reduced the parasitological findings significantly (oocyst excretion and number of lesions) and improved the technical parameters (body weight gain and feed conversion). The highest dosage (20 mg of ponazuril in the feed) showed the best results. This dosage corresponded approximately to a dosage of 3.5 mg/kg of body weight and day.

B. Field Trial of the Efficacy of Ponazuril Compared with Toltrazuril for the Treatment of Natural Infections of Grazing Lambs with Coccidiosis:

| Group (infection/ treatment) | Infection (parasite/route) | Treatment (formulation/ dose) | Stock (species/ number/man- agement) | Parameter |
|---|---|---|---|---|
| 2 groups treated with toltrazuril as drench on day 7 | Infection with *Eimeria* spp. on the pasture (principal species *E. ovinoidalis* and *E. crandallis*)/ natural infection | 5% w/v suspension, 20 mg/kg | Sheep/ 10 to 24 animals per group (159 sheep in total)/field trial | Oocyst excretion, mortality, consistency of the faeces, weight gain |
| 3 groups treated with ponazuril as drench on day 7 | | 5% w/v suspension, 10 and 20 mg/kg | | |
| 3 groups untreated | | | | |

The aim of the trials was to compare toltrazuril and ponazuril for efficacy on natural infections with pathogens of the Eimeria family.

The active ingredients were compared in three consecutive experiments:
  Experiment 1: untreated control—toltrazuril 20 mg/kg—ponazuril 20 mg/kg
  Experiment 2: untreated control—ponazuril 20 mg/kg
  Experiment 3: untreated control—toltrazuril 20 mg/kg—ponazuril 10 mg/kg.

The oocyst excretion and the consistency of the faeces were used as main parameters. The weight of the stock was likewise checked occasionally.

The infection pressure was low during the period of the investigation. Both toltrazuril and ponazuril were completely effective under the test conditions.

C: Efficacy of Toltrazuril and Ponazuril for the Treatment of Experimental Infections of Piglets with *Isospora suis*.

The aim of this trial was to investigate the efficacy of various dosages of toltrazuril and ponazuril for piglet coccidiosis.

2 groups (A and B) of 3-week old piglets were infected on day 0 by stomach tube with $5 \times 10^3$ oocysts of Isospora suis. Group C was kept as infected, untreated control group.

All the groups received toltrazuril or ponazuril as single dose according to their individual body weight on day 3 after the infection.

| | | | | | | | | | MacMaster coprological examination | | | | | | | |
|---|---|---|---|---|---|---|---|---|---|---|---|---|---|---|---|---|
| | Day | | -3 | 0 | 3 | 4 | 5 | 6 | 7 | 9 | 11 | 13 | 15 | 17 | 19 | 21 |
| Group A | I. | 1. | — | — | — | — | — | — | — | — | — | — | — | — | — | — |
| | | 2. | — | — | — | — | — | — | — | — | — | — | — | — | — | — |
| | | 3. | — | — | — | — | — | — | — | — | — | — | — | — | — | — |
| | | 4. | — | — | — | — | — | — | — | — | — | — | — | — | — | — |
| | II. | 1. | — | — | — | — | — | — | — | — | — | — | — | — | — | — |
| | | 2. | — | — | — | — | — | — | — | — | — | — | — | — | — | — |
| | | 3. | — | — | — | — | — | — | — | — | — | — | — | — | — | — |
| | | 4. | — | — | — | — | — | — | — | — | — | — | — | — | — | — |
| Group B | I. | 1. | — | — | — | — | — | — | — | — | — | — | — | — | — | — |
| | | 2. | — | — | — | — | — | — | — | — | — | — | — | — | — | — |
| | | 3. | — | — | — | — | — | — | — | — | — | — | — | — | — | — |
| | | 4. | — | — | — | — | — | — | — | — | — | — | — | — | — | — |
| | II. | 1. | — | — | — | — | — | — | — | — | — | — | — | — | — | — |
| | | 2. | — | — | — | — | — | — | — | — | — | — | — | — | — | — |
| | | 3. | — | — | — | — | — | — | — | — | — | — | — | — | — | — |
| | | 4. | — | — | — | — | — | — | — | — | — | — | — | — | — | — |
| Group C | | 1. | — | — | — | — | — | 0.2 | 0.3 | 4.8 | 38 | 72 | 74 | 78 | 48.8 | 12 |
| | | 2. | — | — | — | — | — | 0.3 | 0.3 | 1.1 | 46 | 98 | 84.6 | 86 | 62.4 | 10 |
| | | 3. | — | — | — | — | — | — | 0.2 | 1.8 | 57.5 | 102 | 98 | 88 | 46.8 | 9.6 |
| | | 4. | — | — | — | — | — | 0.1 | 0.4 | 5.6 | 61 | 144 | 116 | 82.4 | 38.8 | 7.2 |

Group A
I. toltrazuril 10 mg/kg of body weight
II. toltrazuril 20 mg/kg of body weight
Group B
I. ponazuril 10 mg/kg of body weight
II. ponazuril 20 mg/kg of body weight
Group C
no administration Comparison of the Toxicity of a Sulphide (Toltrazuril) with the Corresponding Sulphone (Ponazuril):

The following toxicity data were determined in accordance with OECD/GLP guidelines, in particular OECD 414, 401 and 408. The investigations of the teratogenicity of the compounds was carried out in accordance with the US guidelines—"Teratogenicity study", Guidelines for Registering Pesticides in the U.S.A., U.S. Environmental Protection Agency, Hazard Evaluation: Human and 10 Domestic Animals. U.S. Federal Register, Vol. 43, paragraph 163.83-3, adopted November 1982.

| | Toltrazuril | | Ponazuril | |
|---|---|---|---|---|
| Investigation | Dosage (NOEL) | NOEL mg/kg of body weight | Dosage (NOEL) | NOEL mg/kg of body weight |
| LD50 rat, oral | 1600-5000 mg/kg of body weight | <1000 | >5000 | 5000 |
| Subchronic rat | 0, 15, 60, 240 ppm | 1.1 | 0, 50, 150, 250, 1000, 4000 ppm | 11.2 |
| Subchronic dog | 0, 1.5, 4.5, 13.5 mg/kg of body weight | 1.5 | 0, 200, 1000, 5000 ppm | 8.3 |
| Teratogenicity rat | 0, 1, 3, 10, 30 mg/kg of body weight | 1.0 | 10, 30, 90, 300 mg/kg of body weight | 90 |
| Teratogenicity | 0, 0.5, 0.75, 1, 2, | 2.0 | 10, 30, 90, | 30 |

|  | Toltrazuril | | Ponazuril | |
|---|---|---|---|---|
| Investigation | Dosage (NOEL) | NOEL mg/kg of body weight | Dosage (NOEL) | NOEL mg/kg of body weight |
| rabbit | 3, 10 mg/kg of body weight | | 300 mg/kg of body weight | |

PREPARATION EXAMPLES

General Preparation Method

The suspensions indicated below can be prepared by the following methods:

The substances are each stirred together until a homogeneous suspension is produced, and the pH is adjusted to a desired range. The bentonite or sodium alginate suspension stabilizer is macerated where appropriate at about 80 or about 40° C. respectively. After preparation of the suspension it can be dispensed into suitable containers.

The amounts are indicated in the formulas in each case in grams [g].

Example 1

Suspension

| | |
|---|---|
| Ponazuril microfine | 10.0 |
| Polyoxyl-35-castor oil | 5.0 |
| Methyl p-hydroxybenzoate | 0.075 |
| Propyl p-hydroxybenzoate | 0.025 |
| Sodium carboxymethylcellulose | 1.0 |
| Water demin. | ad 100.0 g |

Example 2

Suspension

| | |
|---|---|
| Ponazuril microfine | 1.0 |
| Methyl p-hydroxybenzoate | 0.075 |
| Propyl p-hydroxybenzoate | 0.025 |
| Sodium alginate* | 1.0 |
| Water demin. | ad 100.0 g |

*Macerated at 40° C.

Example 3

Suspension

| | |
|---|---|
| Ponazuril microfine | 50.0 |
| Bentonite** | 3.5 |
| Xanthan | 3.0 |
| Dioctyl sodium sulphosuccinate | 2.5 |
| Simethicone emulsion | 1.0 |
| Sodium benzoate | 2.0 |
| Sodium propionate | 2.0 |
| Citric acid powder | 4.0-10.0 |
| 1,2-Propylene glycol | 105.0 |
| Water demin. | ad 1030.0 g |

The pH is adjusted to 3.4 to 4.2 by appropriate metering of citric acid.
**As recommended by the manufacturer, the bentonite is preferably initially heated in aqueous suspension to 80° C. and, after swelling, processed with the other ingredients to a suspension.

The invention claimed is:

1. A method for controlling *Isospora suis* in livestock comprising administering to an animal in need thereof an effective amount of a pharmaceutical composition comprising a compound of the formula (I)

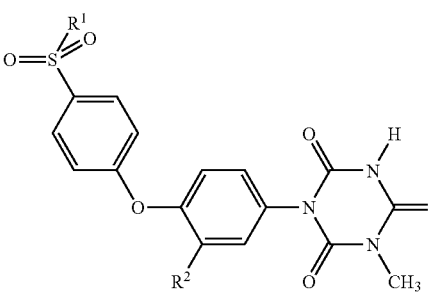

in which
R$_1$ represents halogenoalkyl,
R$_2$ represents alkyl, alkoxy, halogen or SO$_2$N(CH$_3$)$_2$, and their physiologically tolerated salts.

2. The method of claim 1, wherein the compounds of formula (I) according to claim 1 are administered in the form of an aqueous oral suspension.

3. A method for controlling *Isospora suis* in livestock comprising administering to an animal in need thereof an effective amount of a pharmaceutical composition comprising:

A) a compound of formula (I)

$$\text{(I)}$$

[chemical structure: 4-(sulfonyl-R$^1$)phenoxy-phenyl substituted triazinetrione with R$^2$ substituent and N-CH$_3$]

in which
- R$_1$ represents halogenoalkyl,
- R$_2$ represents alkyl, alkoxy, halogen or SO$_2$N(CH$_3$)$_2$, and their physiologically tolerated salts,
in concentrations of from 0.1 to 30% by weight B) suspension stabilizers in concentrations each of from 0.01 to 5% by weight, wherein the suspension stabilizers are a combination of bentonites and xanthan, C) optionally ionic or nonionic wetting agents in concentrations of from 0.01 to 5% by weight, D) optionally antifoams in concentrations of from 0.01 to 5% by weight, E) optionally humectants in concentrations of from 1 to 30% by weight, F) optionally preservatives or combinations thereof in concentrations of from 0.001 to 5% by weight, G) optionally acidic or basic substances in the concentrations necessary to adjust the pH.

\* \* \* \* \*